United States Patent
Chan et al.

(10) Patent No.: US 6,348,192 B1
(45) Date of Patent: Feb. 19, 2002

(54) INTERLEUKIN-2 MUTEIN EXPRESSED FROM MAMMALIAN CELLS

(75) Inventors: Sham-Yuen Chan, El Sobrante; Ruth Kelly, Richmond, both of CA (US)

(73) Assignee: Bayer Corporation, Berkeley, CA (US)

( * ) Notice: Subject to any disclaimer, the term of this patent is extended or adjusted under 35 U.S.C. 154(b) by 0 days.

(21) Appl. No.: 09/310,026

(22) Filed: May 11, 1999

(51) Int. Cl.[7] .................. A61K 38/20; C07K 14/55; C12N 5/16; C12N 15/26; C12N 15/64
(52) U.S. Cl. ............... 424/85.2; 514/2; 514/8; 514/12; 530/351; 435/69.52; 435/325; 435/471; 435/320.1; 435/365.1
(58) Field of Search ................ 530/350, 351; 424/85.1, 85.2; 514/2, 8, 12; 435/69.52, 325, 471, 320.1, 352–372.3

(56) References Cited

U.S. PATENT DOCUMENTS 4,588,585 A * 5/1986 Mark et al. ............... 424/85

FOREIGN PATENT DOCUMENTS

WO    WO 94/01548    *  1/1994

* cited by examiner

Primary Examiner—Prema Mertz
(74) Attorney, Agent, or Firm—Melissa A. Shaw

(57) ABSTRACT

Glycosylated interleukin-2 muteins are described. A method of producing the muteins using mammalian cells is included. The muteins may be incorporated into pharmaceutical preparations useful for, e.g., cancer therapy.

4 Claims, 1 Drawing Sheet

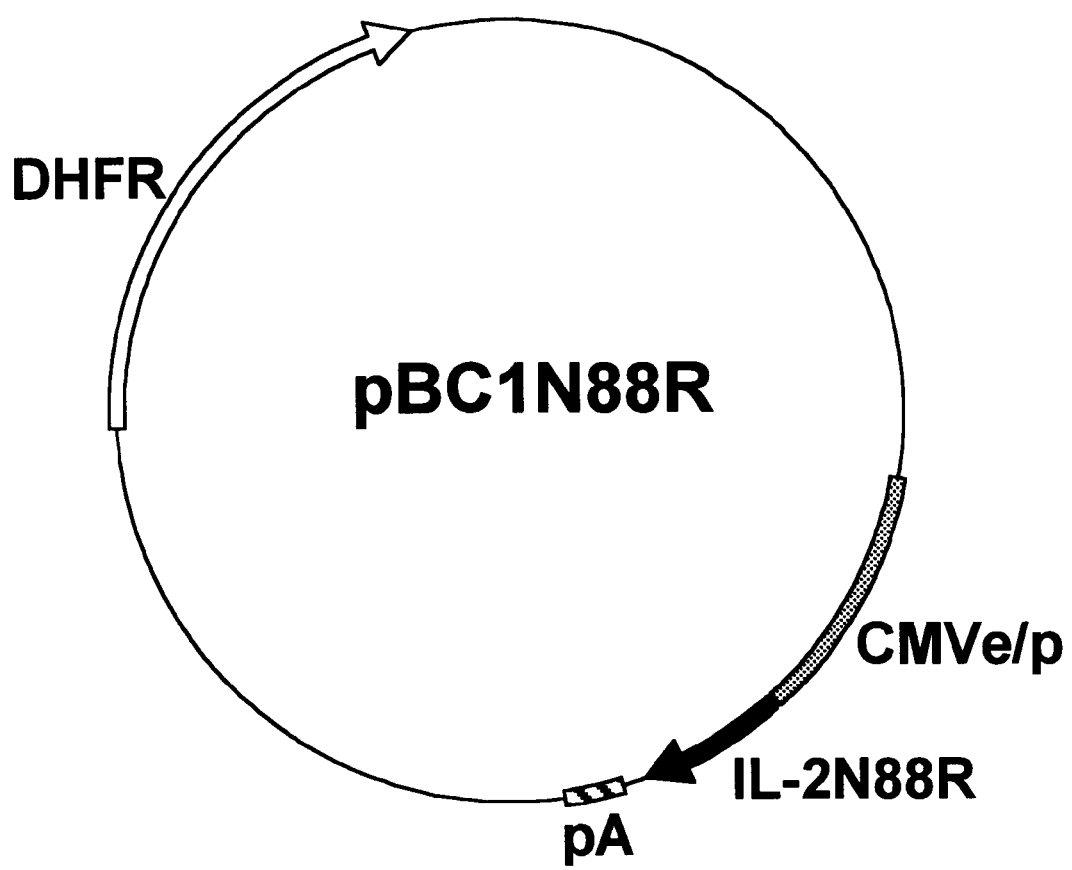

INTERLEUKIN-2 MUTEIN EXPRESSED FROM MAMMALIAN CELLS

RELATED APPLICATION

Related subject matter is disclosed in patent application Ser. No. 09/080,080, entitled "IL-2 Selective Agonists and Antagonists," filed May 15, 1998 in the names of Shanafelt et al., the entirety of which is incorporated herein by reference.

BACKGROUND OF THE INVENTION

1. Field

This invention generally relates to the recombinant production of therapeutic proteins. More specifically, the invention is directed to glycosylated interleukin-2 muteins which can selectively activate T cells (PHA-blasts) and reduce activation of Natural Killer ("NK") cells.

2. Background

The biological activity of a glycoprotein is dependent upon not only the integral structure of the protein, but also the properties of the oligosaccharide covalently attached to the protein. By influencing the physico-chemical and biological properties of proteins, oligosaccharides can modulate the therapeutic effect of a glycoprotein pharmaceutical. It is well recognized that glycosylation can affect solubility, resistance to proteolytic attack and thermal inactivation, quaternary structure, activity, targeting, antigenicity, functional activity, and half-life of the protein. The role of oligosaccharide in determining the in vivo activity of EPO and the half-life of tissue plasminogen activator has been reported.

Proleukin® (interleukin-2) has been approved by the FDA to treat melanoma and renal carcinoma. However, due to the toxic side effects associated with interleukin-2, there is a need for a less toxic IL-2 mutein that allows greater therapeutic use of this interleukin. Although non-glycosylated interleukin-2 has been produced in E. coli with full biological activity, proper refolding of the recovered protein and the potential for altered pharmacokinetics have been areas of concern. It is known that the purification of interleukin-2 derived from E. coil requires the use of chaotropic and toxic agents such as guanidine chloride and urea. Thus it would be advantageous to produce glycosylated IL-2 muteins in mammalian cells where the use of harsh reagents can be avoided.

U.S. Pat. No. 5,417,970 to Roskam et al. (May 23, 1995), incorporated herein by reference, discloses a wild type IL-2 preparation. The above-cited related application of Shanafelt et al. discloses IL-2 muteins and states that the muteins may be expressed in a variety of cells, including microbial, plant, and animal cells, including mammalian cells. We have now found a way to make such IL-2 muteins in glycosylated form from mammalian cells. The characterization and details for making a preferred IL-2 mutein are described below.

SUMMARY OF THE INVENTION

We have developed a method for the production of glycosylated IL-2 muteins from mammalian cells. Preferably the cell host is CHO cells, but the production can be done with other cell hosts including HKB (see U.S. patent application Ser. No. 09/209,920 to Cho filed Dec. 10, 1998, incorporated herein by reference), myeloma, and 293S cells. The production medium is preferably a chemically-defined medium free of plasma protein supplements.

This invention is illustrated with a specific glycosylated polypeptide comprising a human IL-2 mutein numbered in accordance with wild-type IL-2 wherein said human IL-2 is substituted at position 88 with arginine, whereby said mutein preferentially activates T cells over NK cells. The preferred mutein is designated IL-2N88R, using conventional terminology to describe the amino acid substitution of asparagine (N) with arginine (R) at position 88 of wild type IL-2. The nomenclature of the oligosaccharide structures is as described (Fukuda et al, 1994). Mammalian glycosylation patterns are well known and are described in Fukuda et al. (1994), incorporated herein by reference.

This mutein exhibits essentially wild-type IL-2 activity on T cells. This invention is also directed to a method of treating a patient afflicted with an IL-2 treatable condition by administering a therapeutically effective amount of a human IL-2 mutein numbered in accordance with wild-type IL-2 having PHA-blast activating activity but having reduced NK cell activating activity. This method is applicable wherein the IL-2 treatable condition is HIV, cancer, autoimmune disease, infectious disease, vaccine adjuvant in cancer vaccine and conventional vaccine therapy for immune stimulation in the elderly or otherwise immunocompromised, as well as in human SCID patients, or other therapeutic application requiring stimulation of the immune system.

BRIEF DESCRIPTION OF THE FIGURE

The FIGURE is a schematic diagram of the IL-2N88R expression vector showing the sites of the cytomegalovirus early promoter sequence (CMVe/p), the polyadenylation signal sequence (pA), and the dihydrofolate reductase (DHFR) sequence.

EXAMPLE 1

Development of Stable, High-producing CHO Cell Lines That Express IL-2N88R

Stable production cell lines that secrete high quantities of the IL-2N88R mutein were developed by transfecting CHO (dhfr-) cells with the expression vector shown in FIG. 1. The vector was constructed using standard recombinant DNA techniques. The expression vector contains discrete expression cassettes for the IL-2N88R gene and the amplifiable and selectable gene DHFR (dihydrofolate reductase). The IL-2N88R gene codes for a protein having the amino acid sequence given by SEQ ID NO:1. About $1 \times 10^6$ CHO (Chinese hamster ovary) cells were transfected with 10 ug of pBC1N88R (see FIGURE) using LIPOFECTIN™ reagents (Life Technology, Bethesda, Md.) according to manufacturer's instructions. The cells were then selected in the presence of 50 nM methotrexate and grown in DME/F12 media deficient in thymidine and hypoxanthine plus 5% dialyzed fetal bovine serum. Cell populations were screened for IL-2N88R production with a commercial ELISA kit (R & D Systems). The high producing populations were further selected in media containing increasing concentrations of methotrexate (100 to 400 nM methotrexate) and screened for the production of IL-2N88R. Limiting dilution cloning was then applied to derive clones with high and stable productivity. The cloning was done in the absence of methotrexate using standard tissue culture techniques. Mammalian cell culture techniques are well known and disclosed in Freshey (1992), Mather (1998), Hu et al. (1997), and Konstantinov et al (1996), each of which are incorporated herein by reference.

EXAMPLE 2

Serumfree Production of IL-2N88R in a Perfusion Bioreactor

Continuous production of IL-2N88R was done by continuous perfusion fermentation. A 19-liter Wheaton fermenter was inoculated with a stable CHO cell line at $2\times10^6$ cells/ml and perfused at a medium exchange rate of 5 liters/day. The production medium was a DME/F12-based medium supplemented with insulin (10 ug/ml) and $FeSO_4$.EDTA (50 uM). The cell density was maintained at $4\times10^6$ cells/ml. The average daily yield of the fermenter was ~200 mg/day. The production IL-2N88R was stably maintained for 30 days.

EXAMPLE 3

Carbohydrate Analysis of IL-2N88R Produced from CHO Cells

IL-2N88R produced from CHO cells was purified using standard chromatography techniques involving ion exchange, reverse phase, and size exclusion chromatography. The oligosaccharide structures of IL-2N88R were characterized using glycosidases and matrix-assisted laser desorption-ionization mass spectrometry (MALDI-MS).

IL-2N88R was analyzed either directly or after sequential digestion with sialidase, beta-galactosidases and O-glycanase on a MALDI spectrometer in linear mode. The observed molecular mass was compared with calculated molecular mass and the oligosaccharide structures were identified.

The total oligosaccharide pool was released with chemical hydrazinolysis and oligosaccharide mapping was performed by high pH anion-exchange chromatography with a Carbo-Pac PA1 column.

IL-2N88R was found to be glycosylated only with O-linked GalNAc, GalNAc-β-Gal, and GalNAc-β-Gal-α-NeuNAc, of which monosialylated GalNAc-β-Gal was the major oligosaccharide. A minor O-glycosylation site beside the site at Thr-3 was also detected. A summary of the oligosaccharide structures found in IL-2N88R was shown in the Table.

TABLE

Assignment of oligosaccharide structures found in IL-2N88R

| | Structure |
|---|---|
| GalNAc | N-acetylgalactosamine |
| GalNAc-β-Gal | N-acetylgalactosamine-β-galactose |
| GalNAc-β-Gal-α-NeuNAc | N-acetylgalactosamine-β-galactose-α-N-acetylneuraminic acid |

Conclusion

As illustrated in the above examples, we have developed a method for the production of IL-2 muteins having a mammalian glycosylation pattern. It is thought that the method may be used to easily produce any IL-2 mutein, using a variety of mammalian cells.

The above examples are intended to illustrate the invention and it is thought variations will occur to those skilled in the art. Accordingly, it is intended that the scope of the invention should be limited only by the claims below.

REFERENCES

Cho, M-Y (1998) U.S. patent application Ser. No. 09/209,920 filed Dec. 10, 1998.

Freshey, R. I. (ed) (1992) Animal Cell Culture: A Practical Approach, 2nd ed. IRL Press, Oxford, England.

Fukuda et al. (1994) Molecular Glycobiology, IRL Press, New York

Hu, W. S., et al. (1997) Large-scale Mammalian Cell Culture, Curr Opin Biotechnol 8: 148–153

Konstantinov, K. B., et al. (1996) Control of long-term perfusion Chinese hamster ovary cell culture by glucose auxostat, Biotechnol Prog 12: 100–109

Liu (1992) Trends in Biotechnology 10: 114–120

Mather, J. P. (1998) Laboratory Scaleup of Cell Cultures (0.5–50 liters), Methods Cell Biology 57: 219–527

Roskam et al. U.S. Pat. No. 5,417,970 (May 23, 1995)

Shanafelt et al. (1998) U.S. patent application Ser. No. 09/080,080 filed May 15, 1998.

---

What is claimed is:

1. An interleukin-2 mutein having a mammalian glycosylation pattern, wherein the interleukin-2 mutein is numbered in accordance with wild-type interleukin-2 and the asparagine at position 88 of the wild type interleukin-2 is substituted with arginine.

2. The mutein of claim 1 wherein the glycosylation is O-linked.

3. The mutein of claim 2 wherein the gylcosylation comprises O-linked GalNAc, GalNAc-β-Gal, and GalNAc-β-Gal-α-NeuNAc.

4. A pharmaceutical preparation comprising the mutein of claim 3 without a toxic solubilizing agent.

* * * * *

SEQUENCE LISTING

<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30
```

-continued

```
Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
             85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Cys Gln Ser Ile
         115                 120                 125

Ile Ser Thr Leu Thr
    130
```